United States Patent [19]

Nelson

[11] Patent Number: 5,074,894
[45] Date of Patent: Dec. 24, 1991

[54] APPARATUS FOR ISOLATING CONTAGIOUS RESPIRATORY HOSPITAL PATIENTS

[75] Inventor: Timothy P. Nelson, Medina, Ohio

[73] Assignee: Component Systems, Inc., Cleveland, Ohio

[21] Appl. No.: 649,465

[22] Filed: Feb. 1, 1991

[51] Int. Cl.$^5$ .............................................. B01D 46/42
[52] U.S. Cl. ........................................ 55/210; 55/97; 55/279; 55/385.2; 55/471; 55/473; 55/DIG. 35; 422/121; 454/252
[58] Field of Search .................... 55/97, 102, 279, 267, 55/385.2, 472, 500, 210, 471, 473, 128, DIG. 35; 98/1.5, 33.1, 2.11, 42.02, 42.04, 42.07, 87; 422/4, 24, 121; 52/79.5; 62/261

[56] References Cited

U.S. PATENT DOCUMENTS

| | | | |
|---|---|---|---|
| 2,784,465 | 3/1957 | Strobel-Fuchs | 55/385.2 X |
| 3,094,400 | 6/1963 | Blanton | 55/102 |
| 3,107,974 | 10/1963 | Potapenko | 422/4 |
| 3,235,325 | 2/1966 | Storchheim | 55/279 X |
| 3,601,031 | 8/1971 | Abel et al. | 98/33.1 |
| 3,774,522 | 11/1973 | Marsh | 98/33.1 |
| 3,937,967 | 2/1976 | Steinitz | 55/102 X |
| 4,045,192 | 8/1977 | Eckstein et al. | 55/222 |
| 4,118,191 | 10/1978 | Bohnensieker | 422/121 X |
| 4,210,429 | 7/1980 | Golstein | 55/279 |
| 4,231,197 | 11/1980 | Caplan et al. | 52/36 |
| 4,252,054 | 2/1981 | Bakels | 55/385.2 X |
| 4,489,881 | 12/1984 | Dean et al. | 236/49.1 |
| 4,560,395 | 12/1985 | Davis | 55/276 |
| 4,630,530 | 12/1986 | Eckstrom et al. | 98/2.11 |
| 4,667,579 | 5/1987 | Daw | 98/33.1 |
| 4,707,167 | 11/1987 | Saito et al. | 55/267 |
| 4,732,592 | 3/1988 | Spengler | 55/356 |
| 4,750,917 | 6/1988 | Fujii | 55/6 |
| 4,832,717 | 5/1989 | Peters | 55/473 |
| 4,850,268 | 7/1989 | Saito et al. | 98/33.1 |
| 4,880,581 | 11/1989 | Dastroli et al. | 264/39 |
| 4,902,314 | 2/1990 | Mizukami et al. | 55/97 |
| 4,917,713 | 3/1990 | Helmus | 55/385.2 |
| 4,928,581 | 5/1990 | Jacobson | 98/1.5 |
| 4,976,461 | 12/1990 | Takahashi | 98/2.11 X |

OTHER PUBLICATIONS

Astrocel®, Brochure (Jul. 1984), pp. 1–12.

*Primary Examiner*—Richard L. Chiesa
*Attorney, Agent, or Firm*—Renner, Otto, Boisselle & Sklar

[57] ABSTRACT

An apparatus for isolating contagious respiratory hospital patients to reduce the nosocomial and airborne transmission of diseases such as tuberculosis, pertussis, influenza and measles is provided. In one embodiment, a self-contained portable and prefabricated room in combination with an air-flow control and filtering system is provided. The room is adapted to be assembled within the confines of a preexisting structure or room such as a hospital room. The air-flow control and filtering system functions to filter air being exhausted from the room to adjoining patient areas and to maintain the room at a continuous negative air pressure relative to ambient atmospheric pressure. The system also automatically increases its capacity when the door is opened in order to maintain a constant negative pressure and further provides a warning system for monitoring unauthorized access to or exit from the room as well as notification of loss of power and/or operation. In another embodiment, a blower unit including a ultraviolet light and HEPA filter is provided which functions to collect, trap and kill pathogens.

18 Claims, 5 Drawing Sheets

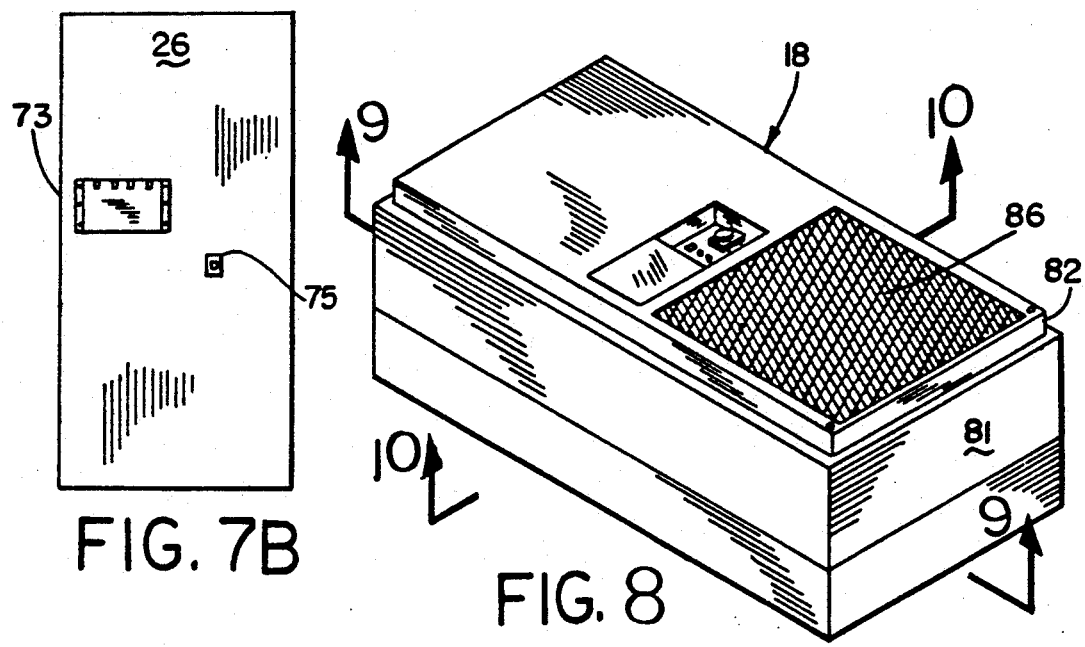
FIG. 7B
FIG. 8
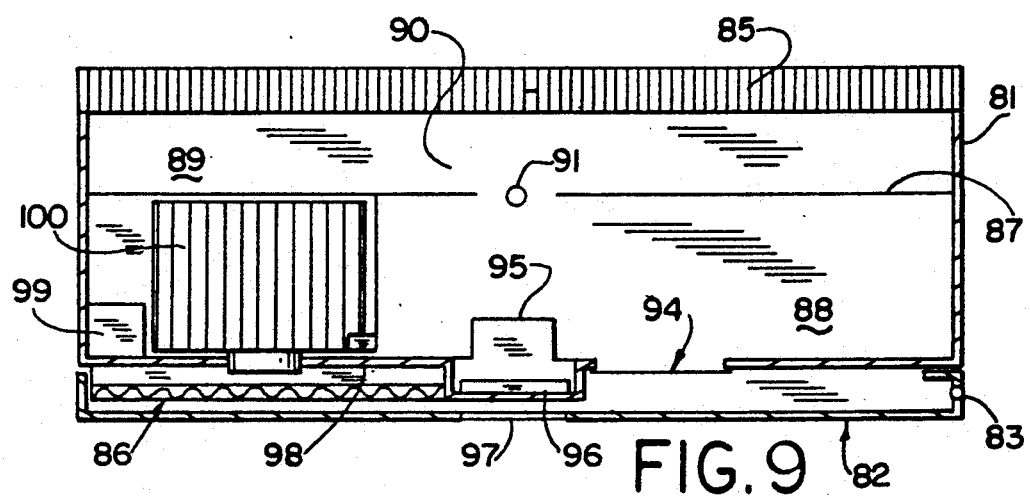
FIG. 9
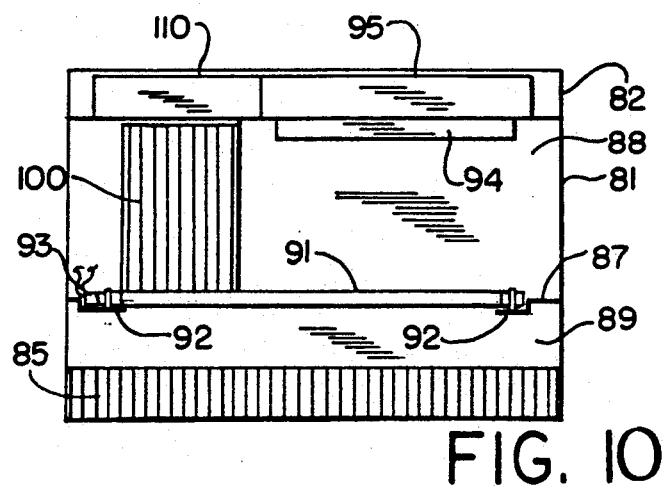
FIG. 10

APPARATUS FOR ISOLATING CONTAGIOUS RESPIRATORY HOSPITAL PATIENTS

TECHNICAL FIELD

This invention pertains to the field of medical isolation rooms, to air-flow control and filtering systems used in such rooms and to related methods thereof. The invention is particularly directed to prefabricated patient isolation rooms equipped with an air-flow control and germicidal filtering system which functions to maintain the air pressure in said room below outside atmospheric pressure and thereby to isolate a patient having an infectious disease.

BACKGROUND OF THE INVENTION

The worldwide HIV virus epidemic has caused respiratory diseases like tuberculosis, pneumonia and influenza also to increase in proportion after years of decrease. Sanitariums previously used for isolating patients with such diseases no longer exist or are very few. Existing hospitals are not well equipped for isolating the patient who has such a disease so as to prevent others from becoming infected. For example, the central heating, ventilating and air-conditioning (H.V.A.C.) systems of such hospitals are generally not designed to provide individual room negative air pressure and those systems that are, will often be old and may function improperly. Dedicating entire wards to these patients and retrofitting existing central H.V.A.C. systems is impractical, cost prohibitive and time consuming. The demographics of these diseases illustrate the largest need for isolation being in densely populated, low-income, urban areas where public health facilities require an especially cost effective method of isolation.

Various portable, patient isolation rooms and air-filtering systems have been developed for isolating patients with high susceptibility to infection. For example, U.S. Pat. Nos. 3,601,031 (Abel et al.) and 3,774,522 (Marsh) describe positive pressure rooms or enclosures which are designed and adapted to be assembled within an ordinary hospital room. Rooms with positive pressure not only allow air to escape but can actually force contaminated air treated by a contagious patient into adjoining rooms through cracks and crevices. Other portable structures, such as the one described in U.S. Pat. No. 4,928,581 (Jacobsen), provide negative pressure, but are constructed from softwall materials that can tear upon impact allowing significant pressure change, allow uncontrolled entry and exit and do not provide wall-mounted utilities within the protected environment.

Fan/filter units, such as those described in U.S. Pat. No. 4,917,713 (Helmus) and U.S. Pat. No. 4,560,395 (Davis), are commonly used in the clean room industry and are designed to provide positive pressure to a room at a manually controlled, fixed speed. However, because uniform air pressure across the filter is desired in clean room applications, internal baffles and chambers within their housings actually increase the surface area available for contaminated particle collection, prior to the filter, with no means of killing pathogens. Automatic compensation for opened doors, notification of pressure or power loss and entry/exit monitoring is also not an integral part or function of these units. Other fan/filter systems, such as that disclosed in U.S. Pat. No. 4,210,429 (Golstein) use high efficiency particulate air (HEPA) filters and germicidal lights to reduce infectious contaminants based upon the principle of recirculation within the room with no change in air pressure, or positive pressure. However, recirculation only creates turbulence within the room and allows contaminated air to escape when doors are opened.

There is a need for negative air pressure rooms that effectively isolate contagious patients and reduce the spread of disease, which can be readily assembled and disassembled within a preexisting structure and adapt to a wide variety of locations.

SUMMARY OF THE INVENTION

The present invention provides a method and apparatus for isolating contagious respiratory hospital patients to reduce the nosocomial and airborne transmission of diseases such as tuberculosis, pertussis, influenza and measles. In one embodiment, a self-contained, portable and prefabricated room in combination with an air-flow control and filtering system is provided. The room is adapted to be assembled within the confines of a preexisting structure or room such as a hospital room. The air-flow control and filtering system functions to filter air being exhausted from the room to adjoining patient areas and to maintain the room at a continuous negative air pressure relative to ambient atmospheric pressure immediately external of the room. The system also automatically increases its capacity when a door to the room is opened in order to maintain a constant negative pressure and further provides a warning system for monitoring unauthorized access to or exit from the room as well as notification of loss of power and/or operation. In another embodiment, a blower unit comprising an ultraviolet light and HEPA filter is provided which functions to collect, trap and kill pathogens.

The isolation rooms of the present invention have the advantage of total prefabrication and simplicity of design. This allows the initial assembly and subsequent disassembly and relocation to be accomplished, in most cases, using relatively unskilled hospital maintenance personnel. Interchangeability of standard components also allows the room to be reconfigured to adapt to a wide variety of locations and size requirements within the hospital. Room component size, durability and washability also facilitate handling and maintenance and enable withstanding the abuse of handling in freight elevators, impact from carts and beds and frequent wash down using chemicals designed for HIV virus, tuberculosis, and disinfection of other pathogens.

Thus, in a broad aspect the present invention relates to a room adapted to be assembled within the confines of a preexisting structure wherein the enclosed room is formed from a plurality of wall panels or other conventional means for prefabricating such rooms. The room is provided with an air-flow control system for maintaining the atmospheric pressure within the room below the atmospheric pressure without or outside the room. Any atmospheric pressure increases within the room are detected by a photohelic pressure switch/gauge or, alternatively, the movement of the door from a closed to an opened condition is detected. This pressure increase or door movement is indicated by conventional means such as a bypass relay or the like and the detected pressure increase or movement is then automatically compensated for in order substantially to maintain the atmospheric pressure within the room below outside atmospheric pressure. In stating that the pressure within the enclosed room is "substantially maintained" below outside atmospheric pressure when door movement and/or a pressure increase is detected and indicated, it is intended to mean that any momentary incidence of pressure equilibration whereby air from within the negative pressure room may uncontrollably be released into the outside environment will be minimized by the method and apparatus of the invention.

In another aspect, a blower module including an enclosed housing and an ultraviolet light disposed between two plenum chambers within the housing is provided. The blower module is disposed to draw air through an intake and discharge it through a filter such that air passing through the module is continuously irradiated by the ultraviolet light as it is conducted through the blower module.

BRIEF DESCRIPTION OF THE DRAWINGS

FIGS. 7A and 7B are interior and exterior views, respectively, of a utility wall panel in the patient isolation room of FIG. 1;

FIG. 8 is a perspective view showing a blower module constructed in accordance with the invention;

FIG. 9 is a cross-sectional view of the blower module looking generally in the direction of the arrows 9—9 of FIG. 8;

FIG. 10 is a cross-sectional view of the blower module looking generally in the direction of the arrows 10—10 of FIG. 8;

DETAILED DESCRIPTION OF THE PREFERRED EMBODIMENTS

Figure 1:
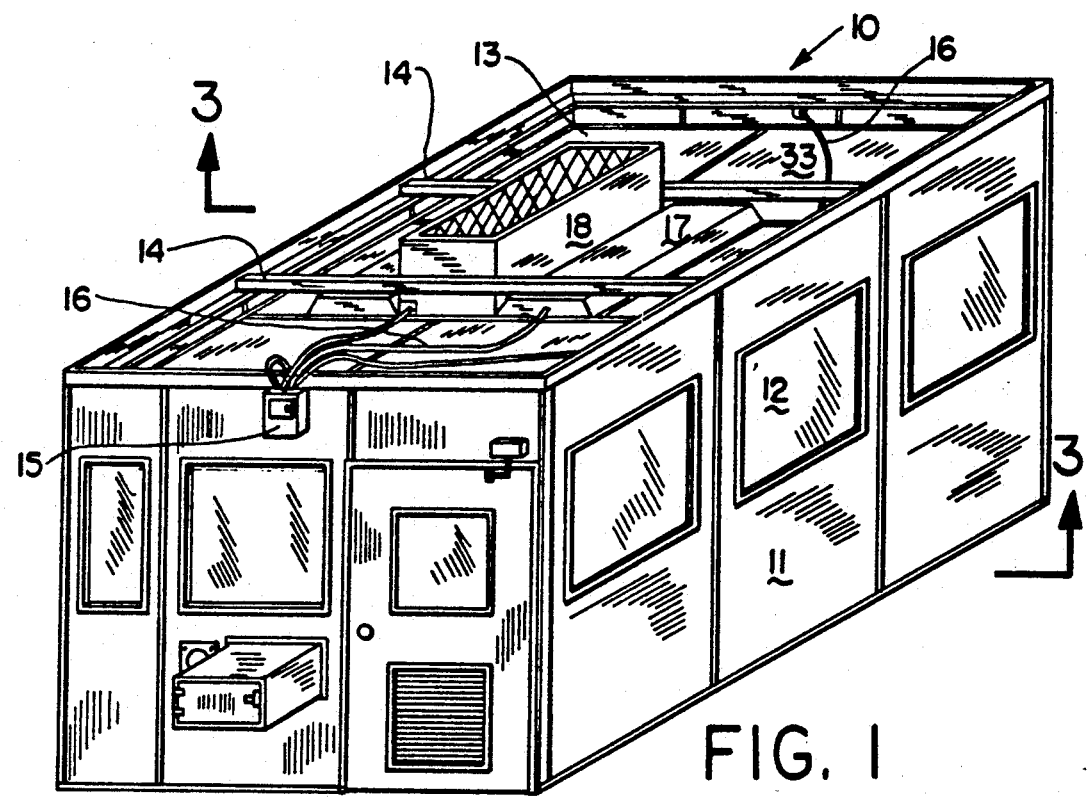
FIG. 1 is a perspective view showing a portable patient isolation room constructed in accordance with one embodiment of the invention.

Referring to the drawings in which like parts are designated by the same reference number in the several figures, FIG. 1 shows one embodiment of a patient isolation room 10 according to the present invention. The room 10 is formed from a plurality of prefabricated wall panels 11 which optionally include a window 12 such as a mar-resistant LEXAN ® window or the like. The prefabricated ceiling 13 is supported by steel support beams 14. The isolation room 10 is connected to a power source, such as a 110 volt AC power source (not shown) via a factory-wired circuit breaker panel 15. The breaker panel 15 is connected to cables 14 via quick connectors (not shown) which distribute power to fluorescent lights 17, blower module 18, and factory-installed electrical switches and electrical receptacles (shown in FIGS. 6A–6B and 7A–7B). The patient isolation room 10 constructed in accordance with the invention is readily assembled within a conventional type of hospital room. The isolation room 10 can normally be assembled and installed in approximately one day. Renovation of the hospital room is held to a minimum since the isolation room itself contains all needed patient support equipment. Utilities such as power, water and oxygen, which are furnished by the hospital, are connected to the room 10 via factory-installed conventional quick connector devices (not shown).

In operation of the isolation room 10 the blower module 18 ordinarily maintains a negative pressure in the room relative to the external atmospheric pressure so that uncontrolled nosocomial and airborne transmission of diseases out from the room will not occur. As is described further below, sealing of various parts of the room 10 also reduces the likelihood of such uncontrolled transmission. Moreover, the blower module 18 can be: (1) manually adjusted with a variable speed control (FIG. 12) to maintain a negative pressure appropriate to the selected room size and (2) automatically adjusted with a bypass relay (FIG. 12) to assure a negative pressure in the room when a condition that would tend to release the negative pressure occurs, such as when the door to the isolation room is opened. Another aspect provided in the room 10 preferably is a means to kill or to inactivate any disease prior to discharge of air to a location external of the room. These features are described in further detail below.

Figure 2:
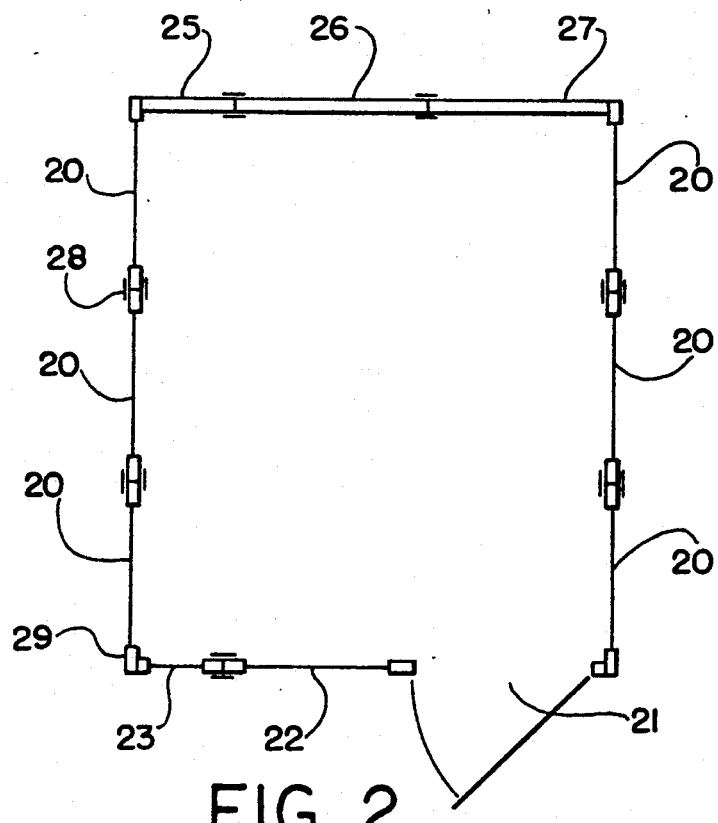
FIG. 2 is a plan view of the patient isolation room shown in FIG. 1.

Referring to FIG. 2 and viewing clockwise in succession from right to left, the portable patient isolator room 10 is constructed or formed of three four-foot window containing panels 20, a door panel 21 (FIGS. 5A–5B), a four-foot pass-through panel 22 (FIGS. 6A–6B), a two-foot window containing panel 23, three additional four-foot window panels 20, a two-foot solid panel 25, a utility panel 26 (FIGS. 7A–7B), and a four-foot solid panel 27. Although the room shown here is 12' by 10', the present invention contemplates rooms in a wide variety of sizes and is therefore not limited to a particular room size. Therefore, more or fewer panels and/or panels of different sizes may be employed. The panels are joined by panel splines 28 (FIG. 4A) and corner posts 29 (FIG. 4B) and are slideably mounted within a top channel 30 (FIG. 3) and a floor channel 31 (FIG. 3) to form the respective walls of the room 10.

Figure 3:
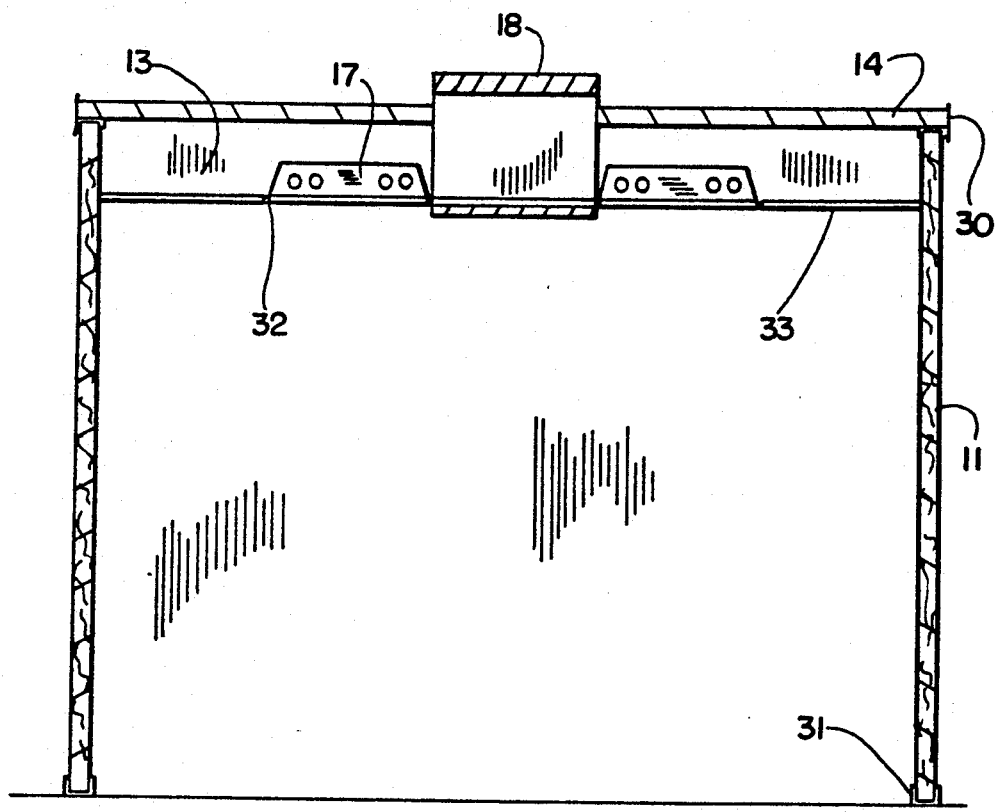
FIG. 3 is a cross-sectional view looking in the direction of the arrows 3—3 of FIG. 1.

Continuing in FIG. 3, an embodiment of the patient isolation room 10 with a prefabricated ceiling 13 is shown which includes a plurality of ceiling panels 32. In this embodiment, the blower module 18 is centrally disposed in the ceiling between sealed layin fluorescent lights 17. Steel support beams 14 extend across the top of the structure and are secured to aluminum top channels 30 to support the suspended ceiling 13. The top and bottom portions of wall panel 11 are secured in top channels 30 and floor channels 31 (4C). A ceiling grid 32 (FIG. 4D) secures ceiling panels 33, fluorescent lights 17 and blower module 18 into the ceiling structure. In an alternate embodiment, the patient isolator room according to the invention uses a preexisting ceiling, e.g., of the preexisting hospital room in which the isolator room 10 is located. In this embodiment top channel 30 is secured directly to the preexisting ceiling and blower module 18 is disposed in one of the wall panels 11.

Figure 4A:
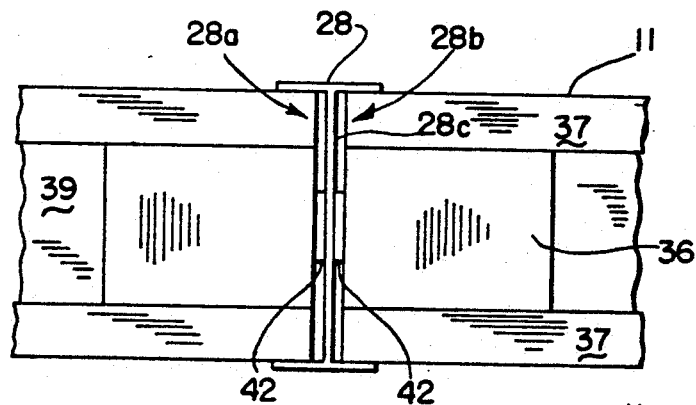
FIGS. 4A, 4B, 4C, 4D and 4E are expanded views of the wall panels and joint assemblies employed in the patient isolator room of FIG. 1.
Figure 4B:
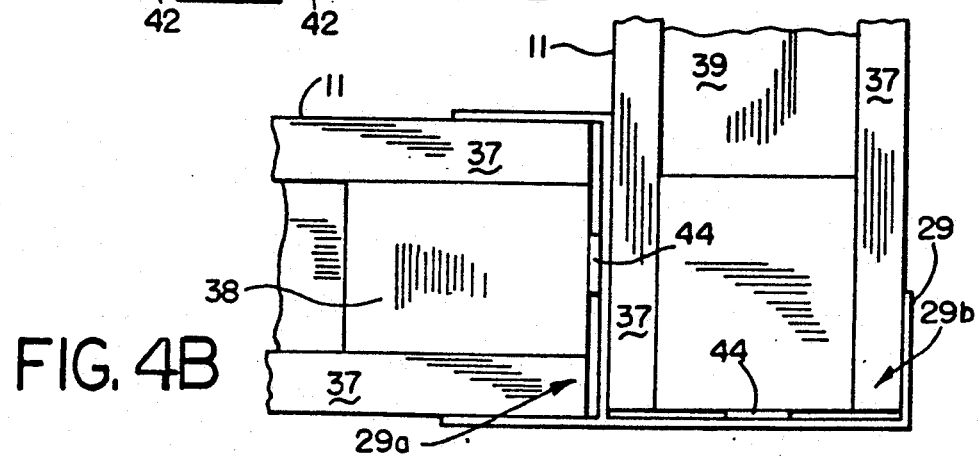
Figure 4C:
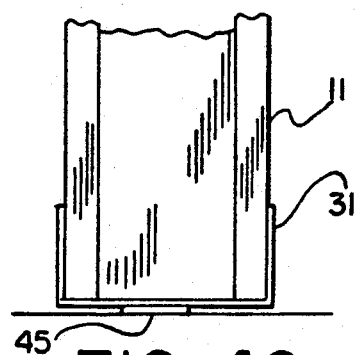
Figure 4D:
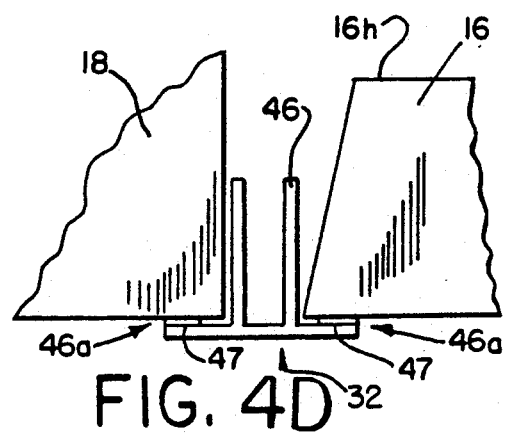
Figure 4E:
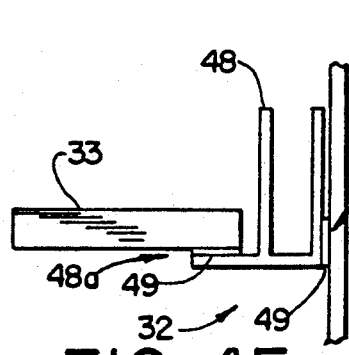

Referring now to FIGS. 4A–4E, the wall panels 11 and joint assemblies between panels and between a panel and another part of the room 10, which are employed in the patient isolator room 10 of FIG. 1, are shown in more detail. Specifically, the wall panels 11 in FIGS. 4A-4C include high-density polystyrene wall studs 36 sandwiched between two plastic laminate surfaced particleboards 37. Such surfaces are particularly suited to withstand frequent antiseptic wash downs without discoloration. Panel cavities 39 may be used to conceal electrical components and wiring. Also, as shown in FIG. 4A, panel splines 28 join wall panels 11. A spline 28 may be metal, plastic or other material that extends the vertical length of the panels 11 and has an I-shape cross section to receive panels in the respective channel portions 28a, 28b on opposite sides of the web 28c. Each joint is sealed with a closed cell PVC gasket 42 that extends along the vertical length of the spline. Similarly, in FIG. 4B, corner sections are formed by joining wall panels 11 with corner posts 29 which are sealed with PVC gasket 44. The corner posts 29 extend the vertical length of the panels as does the gaskets 44, and the corner posts have, for example, the illustrated cross section to receive the respective wall panels in channel portions 29a, 29b. FIG. 4C is an expanded view of the aluminum floor channel 31 adapted to receive wall panel 11. The floor channel 31 is sealed against leakage and secured to the floor with a double-faced PVC gasket tape 45. Similarly, in FIGS. 4D-4E, part of the ceiling grid 32, for example aluminum ceiling grid strip 46 (FIG. 4D), functions to support and to secure the housing 16 for the fluorescent light 16 and blower module 18 into the ceiling 13. Similar ceiling grid strips 46 are used to support and to secure ceiling panels 32. The joints 46a between grid strips and that are being supported thereby are also sealed with a PVC gasket 47. FIG. 4E shows a plastic laminate/particleboard ceiling panel 33 abutting an aluminum ceiling wall angle 48 which makes up part of the ceiling grid 32 adjacent a wall of the room, such as the wall panel 20 shown. The joints 48a between the wall angle 48 and both the wall 20 and the ceiling panel 32 are also sealed with a gasket 49.

Figure 5A:
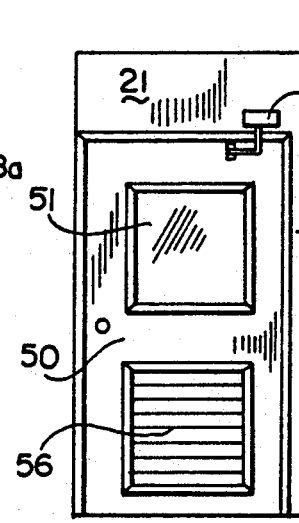
FIGS. 5A and 5B are exterior and interior views, respectively, of the door panel in the patient isolation room of FIG. 1.
Figure 5B:
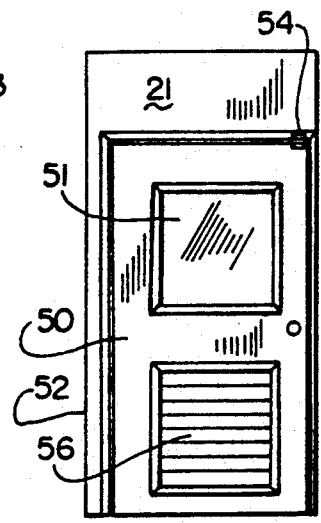

Referring now to FIGS. 5A-5B, door panel 21 includes a plastic laminate faced door 50 with a framed LEXAN® door glass 51 and aluminum door frame 52. The exterior side of the door (FIG. 5A) includes a conventional automatic door closer 53. The interior side of door 50 includes a magnetic door switch 54 (see also FIG. 12 at 125) which is used to detect opening of the door as part of the air-flow control system of the present invention. This can be a Sentrol magnetic switch, Cat. No. 1085T. Optionally, a mechanical switch (not shown) such as a Sentrol Cat. No. 3005 could be used. Door panel 21 also includes an adjustable steel door louver 56 which functions as an air inlet in the air-flow control system of the present invention.

Figure 6A:
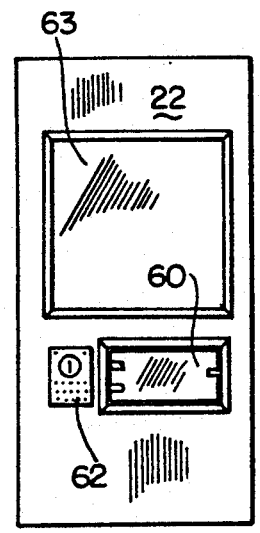
FIGS. 6A and 6B are exterior and interior views, respectively, of a window panel with a food tray pass-through and pressure monitor in the patient isolation room of FIG. 1.
Figure 6B:
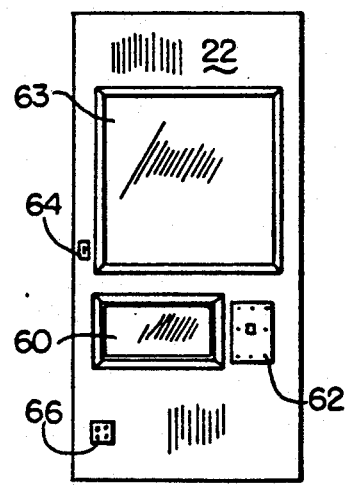

As shown in FIGS. 6A-6B, respective exterior and interior views of an optional prefabricated pass-through panel 22 are described in more detail. The pass-through panel 22 includes a food tray/apparatus pass-through 60 including a hinged LEXAN® door and latch that allows food and other items to be placed in the room without a person entering, i.e., without opening the door 50. Panel 22 also includes a room pressure monitor panel 62 (i.e., a magnahelic gauge or the like) which allows visual monitoring of relative air pressure. Optionally, a photohelic pressure switch/gauge (not shown) such as a Dwyer Series 3000 (Michigan City, Ind.) is used in lieu of gauge 62 to detect pressure changes resulting from the opening of door 50 and tripping a bypass relay (shown in FIG. 12 as 126) to increase airflow as part of the air-flow control system of the present invention. Panel 22 further includes a frame and window 63 such as a LEXAN® window or the like. Interior portion (FIG. 6B) can include a factory-installed three-way electrical light switch 64, and an electrical outlet 66 with quick connect cabling such as FLEX-4® (American Flexible Cable) or the like.

Figure 7A:
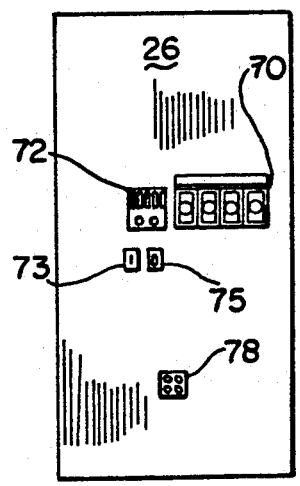

FIGS. 7A-7B show respective interior and exterior views of an optional prefabricated utility panel 26. This panel includes recessed outlet 70 for oxygen, medical air, vacuum and emergency power. An intercom/call station box 72 is disposed adjacent to the recessed outlets 70 on the interior side (7A) of utility panel 26. A light switch 73, modular phone receptacle 75 and a wall receptacle 78 are also provided.

Blower Module

Referring to FIGS. 8-11, the blower module generally indicated at 18 includes a housing 81 enclosed on all four sides, and a steel cover 82 hingedly connected to the housing 81 via hinge 83.

Figure 12:
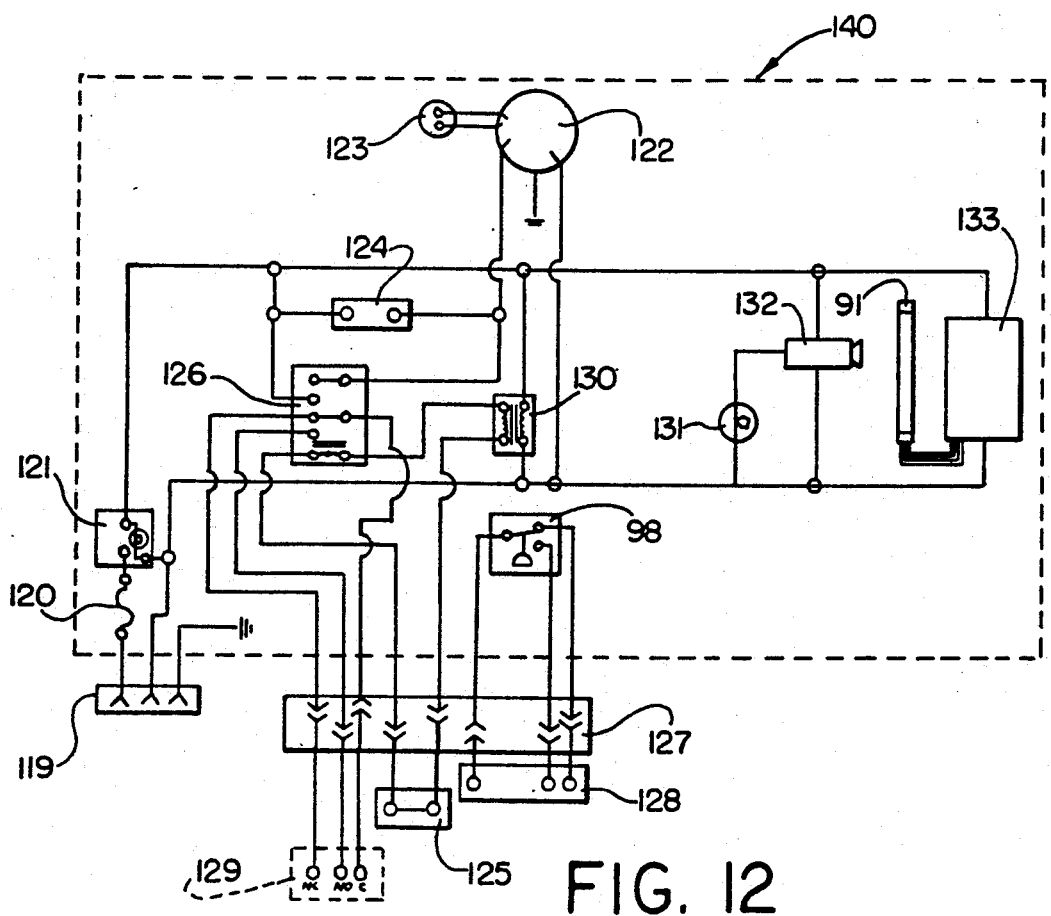
FIG. 12 is a schematic diagram of the electrical system associated with the air-flow control system of this invention.

A replaceable high-efficiency particulate air (HEPA) filter element 85 defines the otherwise open top of the blower module 18. The filter is a conventional item such as, for example, an ULPA filter from Cambridge Filter Co. (Syracuse, N.Y.) with an efficiency of about 99.999% for particles of 0.12 microns or greater. The filter element 85 is primarily responsible for removing the very small particles included in the air flowing therethrough. A pre-filter 86 is also provided, such as a 30% pleated ASHRAE disposable type filter. A central horizontal partition panel 87 separates the interior of the module into a first plenum chamber 88 and a second plenum chamber 89 between the horizontal panel 87 and the HEPA filter element 85. A central opening 90 in the panel 87 provides air flow communication between the two plenum chambers 88, 89. An ultraviolet (U.V.) lamp 91 is mounted in the opening 90. The lamp 91 is positioned in the plenum partition opening 90 such that about one-half resides in the first plenum and about one-half resides in the second plenum. This allows the U.V. lamp 91 to irradiate the HEPA filter element 85 and both plenum chambers where pathogens collect and are trapped. The ultraviolet light produced by lamp 91 is intended to kill pathogens and the like. A particular advantage of the placement of U.V. lamp 91 in opening 90 is that all air going through blower module 18 goes past lamp 91 at close proximity. With the use of the ultraviolet light from the lamp 91, pathogens which reach and become entrapped in the filter 85 are essentially dead or are killed by ultraviolet light which constantly falls on the filter 85 and particles that are not picked up by filtration of the filter 85 are sterilized. The lamp 91 is suitably supported on a conventional light bracket 92 (FIG. 10). The lamp 91 is a conventional item such as, for example, an 18 inch nominal 420 milliamp germicidal lamp such as Catalog No. GPH463T5L/4 from Light Sources, Inc. (Millford, Conn.). The U.V. light connector 93 connects lamp 91 to a suitable ballast such as a Robertson 55-25 ballast (FIG. 12).

There are a number of other components secured in housing 81 including U.V. light access plate 94, control box 95, control panel 96, acrylic lens 97, differential pressure switch 98 and electrical box 99. In this regard, the differential pressure responsive switch 98 monitors plenum 88 pressure and provides warning (either by audible or visual alarm) if power fails, filter 85 or housing 81 is substantially punctured or motor (FIG. 12) breaks causing loss of blower 100. For example, the pressure responsive switch 98 may compare air pressure in the plenum 88 and a reference pressure, such as that in the chamber 101 in which the blower 100 is located. The control panel 96/box 95 contains an on/off switch, fuse, U.V. light alarm, motor starter (not shown), variable speed control, bypass/alarm relay and low voltage transformer (see FIG. 12). The clear acrylic lens 97 over the control panel allows visual inspection of alarm lights and prevents unauthorized access to the on/off switch (FIG. 12). The U.V. access plate 94 allows easy changing of the lamp 91.

Figure 11:
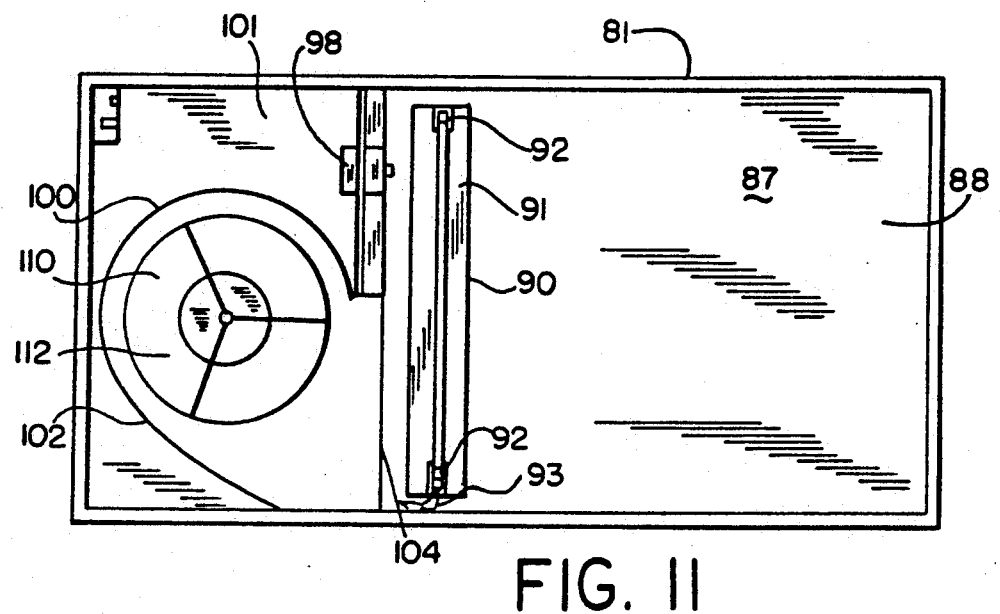
FIG. 11 is a plan view of the blower module of FIG. 8.

A standard motorized centrifugal blower 100 is mounted in a blower chamber 101 at the left end of the housing 81 and blows air, drawn in from the room 10 via the prefilter 86, into first plenum chamber 88, as viewed in FIGS. 9 and 11. The blower includes, for example, a direct drive, forward curve centrifugal-type fan and a ⅓ Hp motor. The blower 100 should be capable of moving up to about 960 cubic feet of air per minute (CFM). It may be other sizes as required by room 10 volume, etc. The outer periphery of blower housing 102 of the blower 100 has a spiral configuration which terminates in the exhaust opening 104. Operation of the blower thus induces a relatively high-velocity flow of air from left to right, as viewed in FIG. 11. This relatively high-velocity airflow is conducted into the first plenum chamber 88. Because the U.V. lamp 91 is mounted in between the first plenum chamber 88 and the second plenum chamber 89, pathogens in the airstream are forced past the U.V. lamp 91 at close proximity for irradiation. Pathogens that are not killed are trapped in filter 85 and continuously "bathed" with U.V. light to kill them which greatly lessens the likelihood of the spread of pathogens.

The air intake to the blower 100 enters from above through the preliminary filter 86 supported by a frame generally indicated at 110 (FIG. 10). This defines an intake opening into the blower module 18 as noted above. Steel cover 82 extends at least partially across the top of the module to provide support for the prefilter 86 and limits access to the control box 95 and control panel 96. The illustrated blower module 18 has been found to perform very effectively with exterior dimensions approximately four feet long, two feet wide, and an overall height of approximately sixteen inches. The blower 100 is often referred to as a centrifugal blower and, for example, can have a diameter of about twelve inches, and an axial length of about six inches. This unit preferably rotates at approximately 1075 RPM, driven at about one-third horsepower. This allows a fan output ranging from about 400 CFM to about 960 CFM.

The height of the first plenum chamber 88 is preferably approximately twice that of the second plenum chamber 89. Several advantages inure to this relationship, for example, including close proximity of the U.V. lamp 91 to HEPA filter 85. The diameter of the opening 90 bridged by the U.V. lamp 91 is about 6½ inches wide and about 19¼ inches long (i.e., approximately 126¾ square inches).

A particular advantage of the present invention is the airflow control system which coordinates blower speed with door traffic to reduce the likelihood of uncontrolled nocosomial or airborne transmission of pathogens outside the room. In normal operation, the air-flow control and filtering system is effective to maintain the isolator room 10 at a negative pressure relative to outside ambient atmospheric pressure by drawing air at from about 400 to about 600 cubic feet per minute (CFM) through an air inlet (such as louver 56) when the door 50 is closed. This provides about twenty to about fifty air changes per hour in the room when the door 50 is closed. According to the invention, a magnetic or mechanical door switch 54 (FIG. 5B) will detect when the door 50 (FIGS. 5A-B) is opened. In an alternate embodiment, a photohelic pressure switch/gauge (not shown) detects the pressure change caused by the opening of door 50. In either case, the detection of door movement is indicated by a bypass relay (FIG. 12) which automatically increases fan output to about 960 CFM in order to substantially maintain the room at a negative pressure relative to outside ambient air pressure. This increased fan output, i.e., blower speed, provides about 100 air changes per hour in the room 10. The advantage of this system is a reduction in the nocosomial or airborne transmission of disease by reducing incidence of positive airflow out of room 10.

Referring now to FIG. 12, there is shown a schematic diagram of the electrical portion of the air-flow control and germicidal filtering system. Many of the components shown in FIG. 12 have been discussed previously with regard to FIGS. 1-11. The power coupled by way of modular wiring block 119 couples through a 15 amp fuse 120 to an illuminated on/off switch 121. The speed of motor 122 (which turns the blower 100), which is shown connected to a motor capacitor 123, can be manually controlled with a conventional variable speed control 124 (e.g., a potentiometric, solid state SCR transistor, etc., or other control). As noted above, the motor 122 also can be automatically controlled when the door switch 125 detects opening of the door. The detection is indicated by way of the bypass relay 126 (e.g., a double pole—double throw 24 V relay) which bypasses variable speed control 124 to automatically increase the speed of motor 122. The door switch 125 is connected to relay 126 via low-voltage wiring block 127. Other components connected to the low voltage block 127 include a power/fan loss alarm 128, the differential pressure switch 98 (FIG. 11), and an optional entry/exit alarm 129 These items are powered by the transformer 130 (e.g., a 120 V A.C. to 24 V A.C. transformer). Also shown in FIG. 12 are control panel light 131 (indicating that the U.V. light is on), a U.V. light sensor 132, the U.V. light 91 (FIGS. 9-11) and U.V. ballast 133.

Operation of the isolator room 10 with the blower module 18 under control of the circuitry 140, which is depicted in FIG. 12, is described and is summarized here. The power switch 121 would be manually closed to supply power to the blower module 18 for operation purposes. The illuminated portion or lamp in the switch 121 would indicate that power is on. Ordinarily, with the door 50 closed, the bypass relay 126 will be in a position to allow power to be fed to the motor 122 via or under control of the variable speed control 124. The variable speed control 124 would be manually adjusted during set up of the circuit 140 so that the motor 122 then would be operating at the desired speed to obtain the desired blower output or airflow. However, when the door switch 125 senses that the door is being opened or actually is in open condition, the bypass relay 126 automatically indicates this condition by energizing and closing the circuit which bypasses the variable speed control 124. Then the motor 122 is operated at a higher velocity, for example, a maximum velocity or a lower than maximum velocity that is determined by a non-variable control (not shown). Closing of the door 50 would be sensed by the door switch 125, which then would operate the bypass relay 126 to open the just-mentioned circuit and enable the motor 122 then to operated under control of the variable speed control 124.

Local power is supplied to the U.V. lamp 91 via a transformer 130 and the ballast 133 to energize the lamp 91 whenever power is supplied the circuit 140 and especially to the blower motor 122. The U.V. light sensor 132 is positioned to detect whether or not U.V. light is being produced by the U.V. lamp 91. If the U.V. lamp 91 is not producing U.V. light, then the sensor 132 operates the control panel light 131 to provide an indication that there is failure in the U.V. lamp 91. The differential pressure sensing switch 98 is operable to control energization or not of the alarm 128, depending on the differential pressure sensed by the switch 98. Power to the alarm 128 would be provided via an external power sample, not shown under control of the switch 98.

Thus, it will be appreciated that the circuit 140 provides for operation of the various components of the blower module 18 to provide for the desired negative pressure condition in the isolator room 10 and to provide for decontamination, killing, sterilizing, etc. functions achieved using the U.V. lamp 91, as the various filters employed in the invention provide for effective filtering of the various particles and pathogens, etc. Moreover, by providing the ability automatically to increase blower speed when the door is opened or possibly even when some other loss of pressure may occur in the room, such as opening of the passthrough, breaking of a window in the room, etc. (the same being sensed, for example, by a pressure sensing switch located in the room or some other similar means), substantial assurance that the atmosphere of the isolator room 10 will not mix with the atmosphere external of the isolator room 10 without first being transmitted through the blower module 18 ordinarily would be assured.

The invention has been described with reference to preferred embodiments. Obviously, modifications and alterations will occur to others upon reading and understanding of the specification. It is intended to include all such modifications insofar as they come within the scope of the appended claims or equivalence thereof.

What is claimed is:

1. A portable room for isolating patients having a contagious disease comprising:
   means for forming an enclosed room;
   door means for providing access between the interior and exterior of said room, said door means being moveable between an opened condition and a closed condition;
   an air inlet in said room;
   an air outlet in said room;
   means for filtering air in said room;
   air-conveying means for drawing air into said inlet and expelling air through said filter means and out of said outlet at a first flow rate sufficient to maintain the atmospheric pressure within said enclosed room below the atmospheric pressure without said room when said door means is in its closed condition;
   means for detecting the movement of said door means from a closed condition to an open condition;
   means for indicating the detection of said movement; and
   means for automatically increasing said first flow rate to an increased second flow rate when said detected movement is indicated, said second flow rate being sufficient to substantially maintain the atmospheric pressure within said enclosed room below the atmospheric pressure without said room when said door means is in its open condition.

2. A portable room according to claim 1 wherein said means for forming an enclosed room comprises a plurality of wall panels being cooperatively engaged to form said room.

3. A portable room according to claim 1 wherein the means for detecting the movement of said door comprises a magnetic door switch.

4. A portable room according to claim 1 wherein said means for detecting the movement of said door comprises a photohelic pressure switch/gauge.

5. A portable room according to claim 1 wherein said means for detecting the movement of said door comprises a mechanical door switch.

6. A portable room according to claim 1 wherein said means for indicating the detection of said movement comprises a bypass relay.

7. A portable room according to claim 1 wherein said first flow rate is sufficient to provide at least twenty air changes per hour within said room.

8. A portable room according to claim 1 wherein said second flow rate is sufficient to provide at least 100 air changes per hour within said room.

9. A portable room according to claim 1 which further comprises an ultraviolet light means associated with both said air outlet and said filtering means.

10. A portable room according to claim 1 wherein said filtering means comprises a HEPA filter capable of filtering particles of about 0.12 microns or greater at 99.999% efficiency.

11. In combination with a room for isolating patients having a contagious disease, having a ceiling, a plurality of wall panels, one of the panels having a door, the door moveable between an open condition and a closed condition; an air-flow and filtering system having a variable flow rate within the room comprising:
   an air filtration module including a housing having first and second end portions and substantially closed sidewall portions;
   an intake opening in said first end portion and an exhaust opening in said second end portion;
   means in said housing positioned to support a first filter unit adjacent said intake opening and a second filter unit adjacent said exhaust opening;
   a horizontal central panel secured in said housing, and separating the space defined by said housing into a first plenum chamber adjacent said first end portion and a second plenum chamber adjacent said second end portion, said horizontal panel having a central opening providing communication between said first and second plenum chambers;
   ultraviolet light means mounted in said central opening such that about one-half resides in said first plenum chamber and about one-half resides in said second plenum chamber;
   blower means mounted in said first plenum chamber beside said central opening and disposed to draw air through said intake opening and discharge said air into said housing and through said exhaust opening such that exhaust from said blower means is continuously irradiated by said ultraviolet light means as it is conducted into said first plenum chamber, through said central opening and out said exhaust opening;

said blower means being capable of drawing air through said intake opening and discharging air through said exhaust opening at a first flow rate sufficient to maintain the atmospheric pressure within said room below the atmospheric pressure without said room when said door is in its closed condition;

means for detecting the movement of said door from a closed condition to an open condition;

means for indicating the detection of said movement; and means for automatically increasing said first flow rate to an increased second flow rate when said detected movement is indicated, said second flow rate being sufficient to substantially maintain the atmospheric pressure within said room below the atmospheric pressure without said room when said door is in its open condition.

12. An air-flow and filtering system according to claim 11 wherein the means for detecting the movement of said door comprises a magnetic door switch.

13. An air-flow and filtering system according to claim 11 wherein said means for detecting the movement of said door comprises a photohelic pressure switch/gauge.

14. An air-flow and filtering system according to claim 11 wherein said means for detecting the movement of said door comprises a mechanical door switch.

15. An air-flow and filtering system according to claim 11 wherein said means for indicating the detection of said movement comprises a bypass relay.

16. An air-flow and filtering system according to claim 11 wherein said first flow rate is sufficient to provide at least twenty air changes per hour within said room.

17. An air-flow and filtering system according to claim 11 wherein said second flow rate is sufficient to provide at least 100 air changes per hour within said room.

18. An air-flow and filtering system according to claim 11 wherein said filtering means comprises a HEPA filter capable of filtering particles of 0.12 microns or greater at 99.999% efficiency.

* * * * *